(12) United States Patent
Cao et al.

(10) Patent No.: US 10,628,974 B2
(45) Date of Patent: Apr. 21, 2020

(54) SYSTEM AND METHOD FOR COMPUTED TOMOGRAPHY

(71) Applicant: SHANGHAI UNITED IMAGING HEALTHCARE CO., LTD., Shanghai (CN)

(72) Inventors: Wenjing Cao, Shanghai (CN); Stanislav Zabic, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 123 days.

(21) Appl. No.: 16/010,507

(22) Filed: Jun. 17, 2018

(65) Prior Publication Data

US 2018/0365870 A1  Dec. 20, 2018

Related U.S. Application Data

(63) Continuation of application No. 15/316,886, filed as application No. PCT/CN2016/082829 on May 20, 2016, now Pat. No. 10,002,447.

(51) Int. Cl.
| | | |
|---|---|---|
| G06K 9/00 | (2006.01) | |
| G06T 11/00 | (2006.01) | |
| A61B 6/03 | (2006.01) | |
| G01N 23/046 | (2018.01) | |
| A61B 6/00 | (2006.01) | |
| G06T 5/00 | (2006.01) | |
| G06T 5/20 | (2006.01) | |
| G06T 5/50 | (2006.01) | |

(52) U.S. Cl.
CPC ............ *G06T 11/008* (2013.01); *A61B 6/032* (2013.01); *A61B 6/5205* (2013.01); *A61B 6/5211* (2013.01); *G01N 23/046* (2013.01); *G06T 5/002* (2013.01); *G06T 5/20* (2013.01); *G06T 11/003* (2013.01); *G06T 11/006* (2013.01); *G01N 2223/401* (2013.01); *G01N 2223/419* (2013.01); *G06T 5/50* (2013.01); *G06T 2207/10081* (2013.01); *G06T 2207/20224* (2013.01); *G06T 2211/421* (2013.01); *G06T 2211/424* (2013.01)

(58) Field of Classification Search
None
See application file for complete search history.

(56) References Cited

U.S. PATENT DOCUMENTS

| | | | |
|---|---|---|---|
| 5,164,670 A * | 11/1992 | Szalma | G01R 33/4625 |
| | | | 324/309 |
| 6,249,595 B1 | 6/2001 | Foxall et al. | |

(Continued)

OTHER PUBLICATIONS

Ziegler, A., et al., Iterative reconstruction of a region of interest for transmission tomography, Medical Imaing 2006: Physics of Medical Imaging, vol. 6142, 1-12 (2006).

(Continued)

*Primary Examiner* — Shervin K Nakhjavan
(74) *Attorney, Agent, or Firm* — Metis IP LLC

(57) ABSTRACT

The present disclosure provides a system and method for CT image reconstruction. The method may include combining an analytic image reconstruction technique with an iterative reconstruction algorithm of CT images. The image reconstruction may be performed on or near a region of interest.

20 Claims, 9 Drawing Sheets

(56) References Cited

U.S. PATENT DOCUMENTS

| | | | | |
|---|---|---|---|---|
| 7,518,114 | B2* | 4/2009 | Ganin | G01T 1/1611 250/363.03 |
| 9,042,626 | B1 | 5/2015 | Katsevich et al. | |
| 2005/0123215 | A1* | 6/2005 | Man | G06T 11/005 382/275 |
| 2009/0190814 | A1* | 7/2009 | Bouman | G06T 11/006 382/131 |
| 2010/0054561 | A1* | 3/2010 | Khare | G06T 11/006 382/131 |
| 2011/0150305 | A1* | 6/2011 | Zeng | G06T 11/005 382/131 |
| 2012/0141006 | A1* | 6/2012 | Koehler | G06T 11/006 382/131 |
| 2013/0114872 | A1 | 5/2013 | Chen et al. | |
| 2013/0284939 | A1* | 10/2013 | DeMan | A61B 6/032 250/393 |
| 2014/0005544 | A1* | 1/2014 | Zalev | A61B 5/0095 600/440 |
| 2015/0146952 | A1* | 5/2015 | Hashizume | G06T 11/005 382/131 |
| 2016/0135774 | A1* | 5/2016 | Ono | A61B 6/5205 378/5 |
| 2016/0163073 | A1 | 6/2016 | Grass et al. | |
| 2016/0163606 | A1 | 6/2016 | Yong et al. | |
| 2016/0242721 | A1* | 8/2016 | Zou | A61B 6/5205 |

OTHER PUBLICATIONS

Tang Jie et al., Dose reduction using prior image constrained compressed sensing (DR-PICCS), Medical Imaging 2011:Physics of Medical Imaging, 7961(1): 1-8 (2011).

Andy Ziegler et al., Iterative reconstruction of a region of interest for transmission tomography, Medical Physics, 35(4): 1317-1327(2008).

The extended European search report in European Application No. 16815524.0 dated Oct. 25, 2018, 7 pages.

International Search Report in PCT/CN2016/082829 dated Jan. 25, 2017, 5 pages.

Written Opinion in PCT/CN2016/082829 dated Jan. 25, 2017, 4 pages.

Fu, Lin et al., Frequency-Split Iterative Tomographic Reconstruction in Targeted Region-of-Interest, Fully 3D Image Reconstruction in Radiology and Nuclear Medicine(2015).

Ziegler, Andy et al., Iterative reconstruction of a region of interest for transmission tomography, Medical Physics, 35(4): 1317-1327(2008).

* cited by examiner

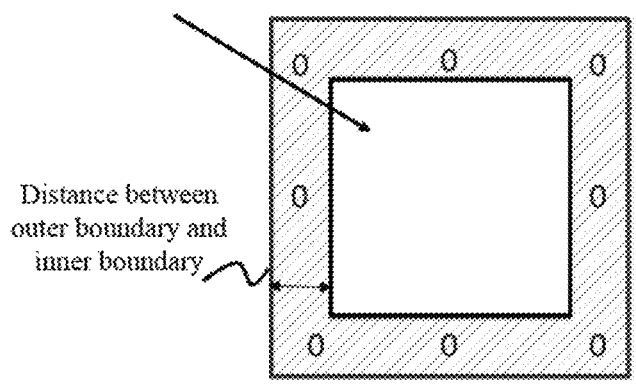
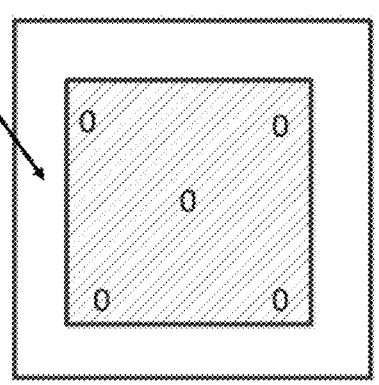
FIG. 10A                FIG. 10B
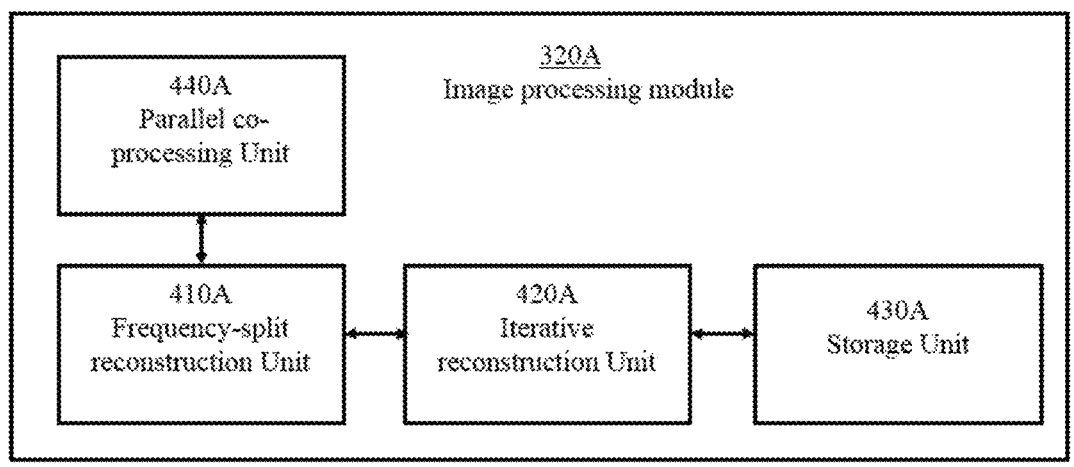
FIG. 11

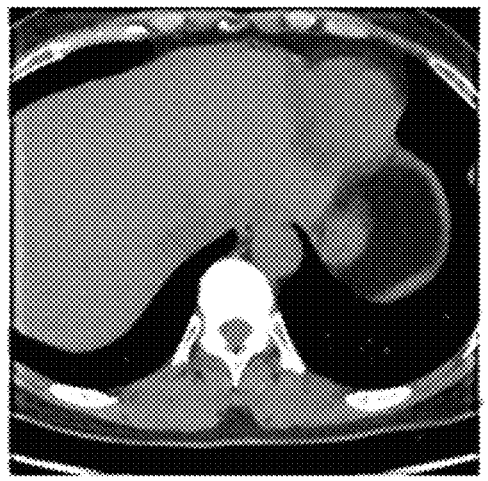
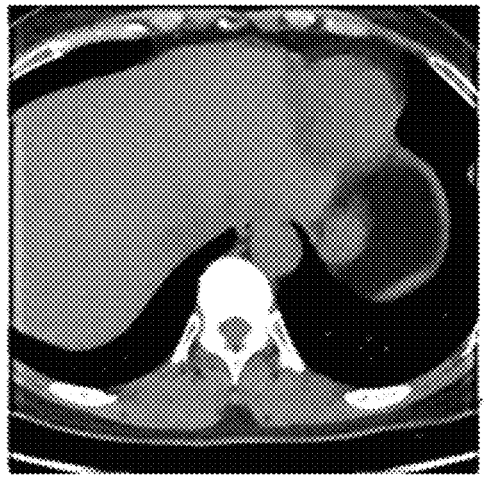
FIG. 13A  FIG. 13B
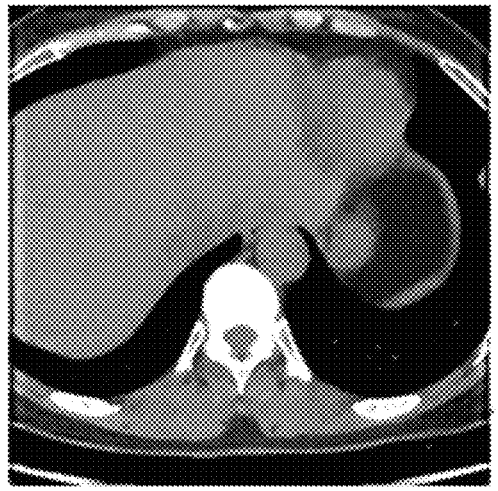
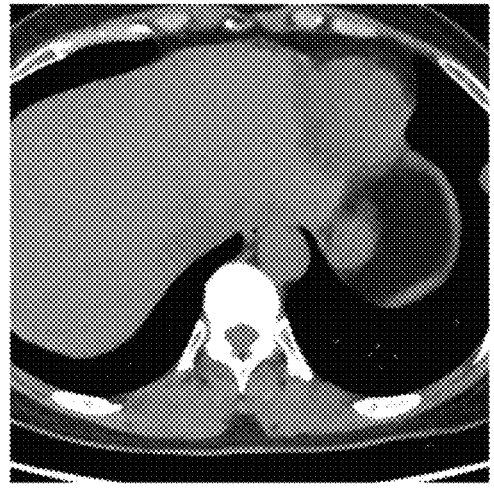
FIG. 14A  FIG. 14B

SYSTEM AND METHOD FOR COMPUTED TOMOGRAPHY

CROSS-REFERENCE TO RELATED APPLICATIONS

This present application is a continuation of U.S. application Ser. No. 15/316,886, filed on Dec. 7, 2016, which is a U.S. national stage under 35 U.S.C. § 371 of International Application No. PCT/CN2016/082829, filed on May 20, 2016, designating the United States of America, the contents of each of which are hereby incorporated by reference.

TECHNICAL FIELD

The present disclosure relates to X-ray computed tomography (CT), and more particularly, relates to a system and method for enhancing CT image reconstruction.

BACKGROUND

Computed tomography (CT) has been widely used in diagnostic and other purposes in the fields of, for example, medicine and other industries. An object, such as a patient, may be scanned with a CT system to obtain CT datasets. For reconstruction of computed-tomographic images from X-ray CT datasets, various reconstruction methods have been developed. These methods may roughly be characterized into two classes: analytical methods and iterative type methods.

Analytic method may be applied directly on X-ray CT datasets, sometimes referred to as raw data, to obtain reconstructed images. On the other hand, iterative reconstruction (IR) methods may achieve better resolution for reconstructed image.

SUMMARY

The present disclosure provided herein relates to X-ray computer tomography (CT). Specifically, the present disclosure relates to a system and method for enhancing CT image reconstruction that may provide improved CT images. The present disclosure provides a system and method for combining an analytic image reconstruction technique with an iterative reconstruction algorithm of CT images. Using this combined approach the processing time may be decreased. Moreover, image reconstruction may be performed on or near a region of interest. The analytic method may be used to produce an initial image for further processing by an iterative reconstruction (IR) algorithm. The low frequency component of an image and the high frequency component of the image may be processed separately, using different image reconstruction methods. As a consequence, the artifacts caused near the boundary of the region of interest may be removed or reduced using the method and system disclosed in the present disclosure.

In an aspect of the present disclosure, an imaging system for obtaining CT images is provided. In some embodiments, the imaging system may include a data acquisition module and an image processing module. The data acquisition module may receive raw data relating to a subject. The image processing module may perform a method including one or more of the operations. A first set of raw data relating to a subject may be received. A first ROI may be determined. A second ROI enclosing the first ROI may be determined. Analytic reconstruction may be applied on the first set of raw data to obtain a first image on the second ROI, and generate a second image by zero padding the first ROI of the first image to be zero. Forward projection may be performed on the first image to obtain a first sinogram. Forward projection may be performed on the second image to obtain a second sinogram. A first filter may be applied on the first sinogram to obtain a third sinogram, followed by subtracting the second sinogram from the third sinogram to obtain a fourth sinogram. A second filter may be applied on the first set of raw data to obtain a fifth sinogram. Based on the fourth sinogram and the fifth sinogram, iterative reconstruction may be performed to generate a third image for the first ROI.

In another aspect of the present disclosure, a method is provide. The method may include one or more of the operations. In a further aspect of the present disclosure, a non-transitory computer readable storage medium including executable instructions is provided. The executable instructions, when executed by a processor, may cause the processor to effectuate a method including one or more of the operations.

In some embodiments, the raw data may include sinogram data.

In some embodiments, the analytic reconstruction may include filter back projection (FBP).

In some embodiments, the region of interest (e.g., the first ROI) may be rectangular, whereas the region enclosing the ROI (e.g., the second ROI) may also be rectangular.

In some embodiments, the ratio of the width to the height of the first ROI may be the same as the width to the height of the second ROI.

In some embodiments, the low-pass filter of the image processing module may be a Gauss filter. In some other embodiments, the low-pass filter may be an atan filter. In some embodiments, the low-pass filter may provide a desired response curve in the frequency domain. In some embodiments, the low-pass filter and the high-pass filter of the image processing module may together form an all-pass filter. A high-pass filter may be obtained by removing the low-pass filter from the all-pass filter.

In some embodiments, the imaging system maybe extended from a Computed Tomography (CT) system, to a Digital Radiography (DR) system, a Computed Tomography-Positron Emission Tomography (CT-PET) system, a Computed Tomography-Magnetic Resonance Imaging (CT-MRI) system, an X-ray security system or an X-ray foreign matter detection system, or the like, or any combination thereof.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The methods, systems, and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIGS. 10A and 10B illustrate an exemplary region of interest and its neighboring area according to some embodiments of the present disclosure;

FIG. 11 is a block diagram of an imaging processing module according to some embodiments of the present disclosure;

FIG. 13A and FIG. 13B are two X-ray images that were generated based on frequency-split iterative reconstruction according to some embodiments of the present disclosure; and FIG. 14A and FIG. 14B are two X-ray images that were generated based on frequency-split iterative reconstruction according to some embodiments of the present disclosure.

DETAILED DESCRIPTION

Figure 1:
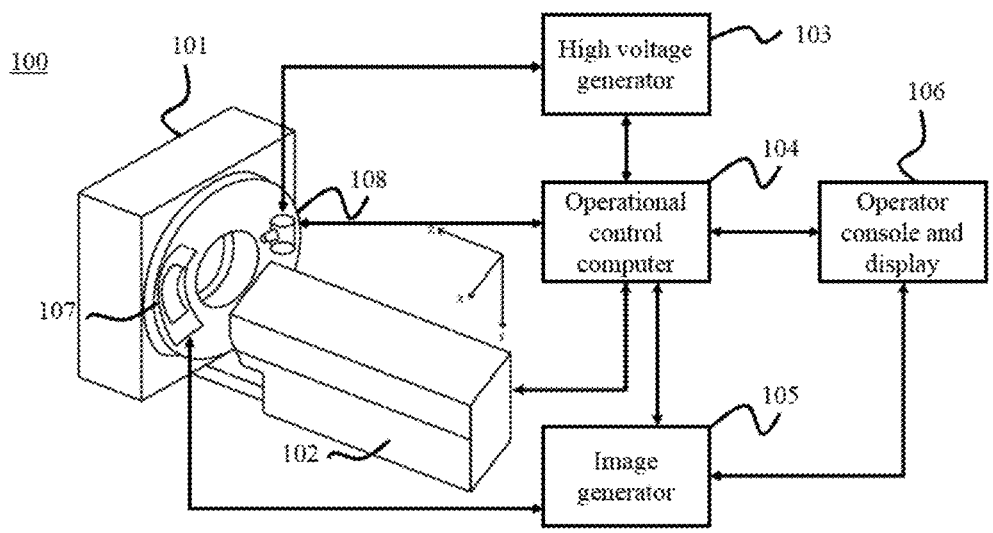
FIG. 1 is a block diagram of an X-ray imaging system according to some embodiments of the present disclosure.

In the following detailed description, numerous specific details are set forth by way of example in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by other expression if they may achieve the same purpose.

It will be understood that when a unit, engine, module or block is referred to as being "on," "connected to" or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof. It will be further understood that the terms "constructed" and "reconstruct", when used in this disclosure, may represent a similar process that an image may be transformed from data.

The present disclosure provided herein relates to X-ray computer tomography (CT). Specifically, the present disclosure relates to a system and method for enhancing CT image reconstruction that may provide improved CT images. The present disclosure provides a way of combining an analytic image reconstruction technique with an iterative reconstruction algorithm of CT images. Using this combined approach the processing time may be decreased. Moreover, image reconstruction may be performed on or near a region of interest, on which the analytic method may be used to produce an initial image for further processing by an iterative reconstruction (IR) algorithm. The low frequency component of an image and the high frequency component of the image may be processed separately, using different image reconstruction methods. As a consequence, the artifacts caused near the boundary of the region of interest may be removed or reduced using the method and system disclosed in the present disclosure.

Merely by way of example, a full field of view (FFOV) may be included in the forward projection to obtain the CT image in the targeted ROI. Within the full field of view, various objects including, for example, a patient's arm(s), a patient bed, a catheter, a pillow, a blanket, may be properly modeled in IR so that reconstruction artifacts may be avoided or reduced. Such an approach of using a full field of view to perform IR may be referred to as a brute-force FFOV-IR.

Besides using a full field of view in the iterative reconstruction of CT images, it may be desirable to design an algorithm using a portion of the full field of view to apply the iterative reconstruction. The portion of the full field of view may be the region of interest. Alternatively, the portion of the full field of view may be a ROI related region related to the region of interest. For example, the ROI related region may contain the region of interest. As another example, the ROI related region may contain the region of interest, and may be similar to the region of interest but up to a scaling factor (see FIG. 10A for an illustration, where the ROI related region is the extended region of interest, whereas the region of interest is the enclosed region in the center. ROI related region and the region of interest may be self-similar with respect to the origin O, and the scaling factor is α).

FIG. 1 illustrates a block diagram of the X-ray imaging system 100 according to some embodiments of the present disclosure. As shown in the figure, the X-ray imaging system 100 may include a gantry 101, an object table 102, a high voltage generator 103, an operational control computer 104, an image generator 105, and an operator console and display 105. It should be noted that the X-ray imaging system described below is merely provided for illustrating an example of a radiation imaging system, and not intended to limit the scope of the present disclosure. The radiation used herein may include a particle ray, a photon ray, or the like, or any combination thereof. The particle ray may include neutron, proton, electron, μ-meson, heavy ion, or the like, or any combination thereof. The photon beam may include X-ray, γ-ray, α-ray, β-ray, ultraviolet, laser, or the like, or any combination thereof. For better understanding the present disclosure, an X-ray imaging system is described as an example of a radiation imaging system. The X-ray imaging system may find its applications in different fields such as, for example, medicine or industry. Merely by way of example, the X-ray imaging system may be a computed tomography (CT) system, a digital radiography (DR) system, a multi-modality system, or the like, or any combination thereof. Exemplary multi-modality system may include a computed tomography-positron emission tomography (CT-PET) system, a computed tomography-magnetic resonance imaging (CT-MRI) system, etc. As another example, the system may be used in internal inspection of components including e.g., flaw detection, security scanning, failure analysis, metrology, assembly analysis, void analysis, wall thickness analysis, or the like, or any combination thereof.

The gantry 101 may house the components necessary to produce and detect X-rays to generate a CT image. The gantry 101 may include an X-ray tube 108 and a detector 107. It should be noted that in alternative embodiments of the present disclosure, the high voltage generator 103 may be located in the gantry 101. The X-ray tube 108 may emit radiation that may be received by the detector 107 after it passes through an object exposed in the aperture of the gantry 101. Merely by way of example, the radiation may include a particle ray, a photon ray, or the like, or any combination thereof. The particle ray may include neutron, proton, electron, μ-meson, heavy ion, or the like, or any combination thereof. The photon ray may include X-ray, γ-ray, α-ray, β-ray, ultraviolet, laser, or the like, or any combination thereof. The object may include a substance, a tissue, an organ, an object, a specimen, a body, a human being, or the like, or any combination thereof. In some embodiments, the X-ray tube 108 may be a cold cathode ion tube, a high vacuum hot cathode tube, a rotating anode tube, etc. The shape of the X-ray beam emitted by the X-ray tube 108 may be a line, a narrow pencil, a narrow fan, a fan, a cone, a wedge, an irregular shape, or the like, or any combination thereof.

The shape of the detector 107 may be flat, arc-shaped, circular, or the like, or any combination thereof. The fan angle of the arc-shaped detector may be an angle from 0° to 360°, or from 30° to 270°, or 45° to 300°. In some embodiments, the fan angle of the arc-shaped detector may be an angle above 30°. In some embodiments, the fan angle of the arc-shaped detector may be an angle above 45°. For example, the fan angle of the arc-shaped detector may be one from 45°, 60°, 75°, 90°, 105°, etc., among other degrees. The fan angle may be fixed or adjustable according to different conditions including, for example, a desired resolution of an image, the size of an image, the sensitivity of a detector, the stability of a detector, or the like, or any combination thereof. In some embodiments, the pixels of the detector 107 may be the number of the detector cells, e.g., the number of scintillator or photosensor, etc. The pixels of the detector may be arranged in a single row, two rows, or another number of rows. The X-ray detector may be one-dimensional, two-dimensional, or three-dimensional.

The high voltage generator 103 may produce high voltage electricity and/or power, and transmit it to the X-ray tube 108. The voltage generated by the high voltage generator 103 may range from 80 kV to 140 kV, or from 120 kV to 140 kV. The current generated by the high voltage generator may range from 20 mA to 500 mA. In alternative embodiments of the present disclosure, the voltage generated by the high voltage generator 103 may range from 0 to 75 kV, or from 75 to 150 kV.

The operational control computer 104 may communicate bi-directionally with the gantry 101, the tube 108, the high voltage generator 103, the object table 102, the image generator 105, and/or the operator console display 104. Merely by way of example, the gantry 101 may be controlled by the operational control computer 104 to rotate to a desired position that may be prescribed by a user via the operator console and display 106. The operational control computer 104 may control the generation of the high voltage generator 103, for example, the magnitude of the voltage and/or the power generated by the high voltage generator 103. As another example, the operational control computer 104 may control the display of images on the operator console and display 106. For instance, the whole or part of an image may be displayed. In some embodiments, an image may be divided into several sub-portions, which may be displayed on a screen at the same time or in a certain order. According to some embodiments of the present disclosure, the user or the operator may select one or more sub-portions to display according to some conditions. Merely by way of example, the user may specify that an enlarged view of a sub-portion is to be displayed.

The operator console and display 106 may be coupled with the operational control computer 104 and the image generator 105. In some embodiments, the operator console and display 106 may display images generated by the image generator 105. In alternative embodiments, the operator console and display 106 may send a command to the image generator 105, and/or the operational control computer 104. Still in alternative embodiments of the present disclosure, the operator console and display 106 may set parameters for a scan. The parameters may include acquisition parameters and/or reconstruction parameters. Merely by way of example, the acquisition parameters may include tube potential, tube current, recon parameters (e.g., slick thickness), scan time, collimation/slice width, beam filtration, helical pitch, or the like, or any combination thereof. The reconstruction parameters may include reconstruction field of view, reconstruction matrix, convolution kernel/reconstruction filter, or the like, or any combination thereof.

The object table 102 may support a patient and move though the aperture of the gantry 101 during an examination. As shown in FIG. 1, the direction of a patient being transmitted during an examination may be along the z direction. Depending on the ROI selected of the patient or the protocols selected, the patient may be positioned supine or prone, and either feet or head first. In some embodiments of the present disclosure, the object table 102 may be indexed between multiple scans. In alternative embodiments of the present disclosure, the object table 102 may be translated through the gantry 101 at a constant speed. The speed may relate to the length of the area to be scanned, the total scan time, the pitch selected, or the like, or any combination thereof. In some embodiments, the object table 102 may be used to support an object other than a patient. Such a structure may move the object for examination through the X-ray imaging system. For brevity, such a structure may also be referred to a patient.

It should be noted that the description of the X-ray imaging system is provided for the purposes of illustration, and not intended to limit the scope of the present disclosure. For persons having ordinary skills in the art, various variations and modifications may be conduct under the teaching of the present disclosure. However, those variations and modifications may not depart from the protecting of the present disclosure. For example, the assembly and/or function of the X-ray imaging system 100 may be varied or changed according to specific implementation scenarios. Merely by way of example, some other components may be added into the X-ray imaging system 100, such as a patient positioning unit, a high-voltage tank, an amplifier unit, a storage unit, an analog-to-digital converter, a digital-to-analog converter, an interface circuit, or the like, or any combination thereof. Merely by way of example, the gantry 101 may further include a microphone, sagittal laser alignment light, patient guide lights, X-ray exposure indicator light, energy stop buttons, gantry control panels, external laser alignment lights, etc.

Figure 2:
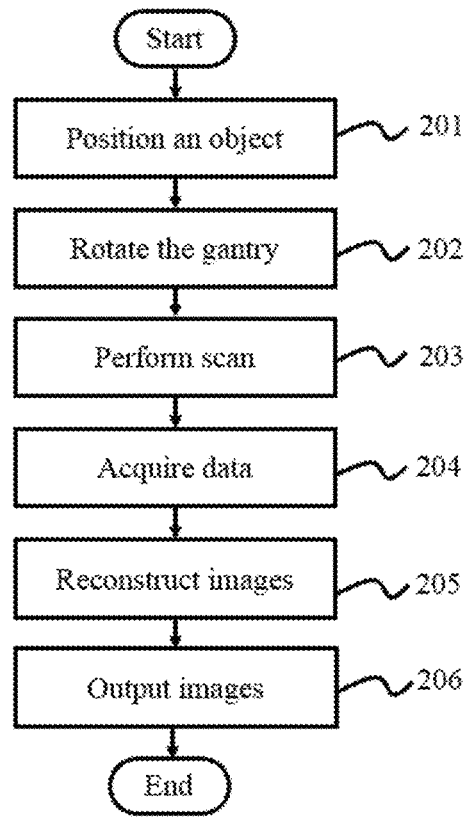
FIG. 2 is a flowchart illustrating a process of a CT scan according to some embodiments of the present disclosure.

FIG. 2 is a flowchart illustrating an imaging process according to some embodiments of the present disclosure. In step 201, an object may be positioned in the X-ray imaging system 100, specifically, on the patient table 102 that is described elsewhere in the present disclosure. Merely by way of example, the object may include a substance, a tissue, an organ, a specimen, a body, or the like, or any combination thereof. In some embodiments, the object may include a head, a breast, a lung, a pleura, a mediastinum, an abdomen, a long intestine, a small intestine, a bladder, a gallbladder, a triple warmer, a pelvic cavity, a backbone, extremities, a skeleton, a blood vessel, or the like, or any combination thereof.

After the object is positioned, the gantry of the X-ray imaging system 100 may be rotated to a desired position in step 202.

In step 203, a scan may be performed on the object. In some embodiments of the present disclosure, a number of protocols may be created for scanning different objects. Multiple parameters may be determined by the protocols. Merely by way of example, the parameters may include a collimator aperture, a detector aperture, X-ray tube voltage and/or current, a scan mode, a table index speed, a gantry speed, a reconstruction field of view (FOV), or the like, or any combination thereof.

By way of the scan, the raw data corresponding to the object may be acquired in step 204.

After the raw data is acquired, the images of the object may be reconstructed in step 205. Merely by way of example, the reconstruction of the images may be based on methods including Fourier slice theorem, filtered back projection algorithm, cone-beam reconstruction (see FIG. 7 for an illustration of cone beam), iterative reconstruction, etc.

The image reconstructed in step 205 may be output in step 206. The output image may undergo further process, such as noise reduction, contrast enhancement, etc.

It should be noted that the flowchart described above is provided for the purposes of illustration, and not intended to limit the scope of the present disclosure. For persons having ordinary skills in the art, various variations and modifications may be conduct under the teaching of the present disclosure. However, those variations and modifications may not depart from the protecting of the present disclosure.

Figure 3:
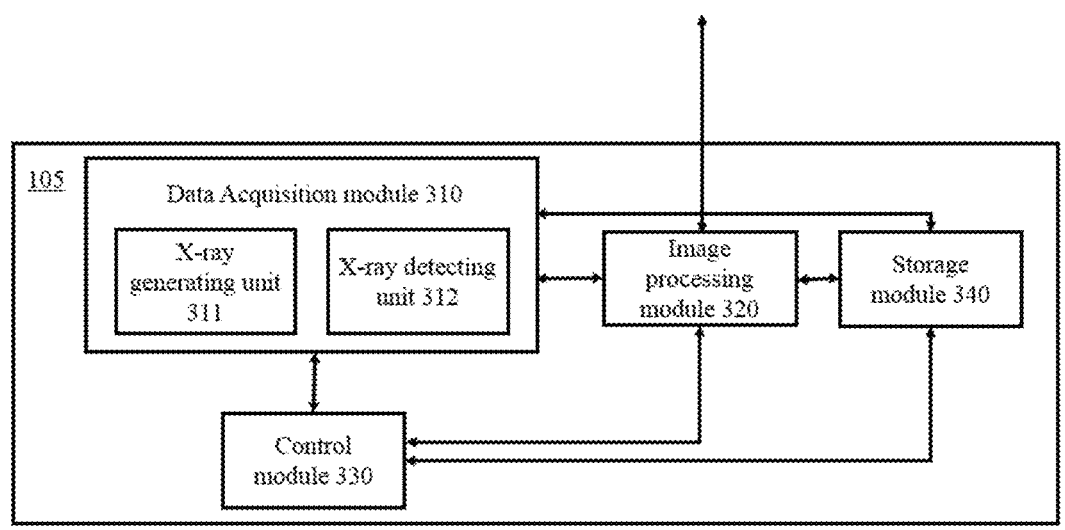
FIG. 3 is a block diagram of an image generator according to some embodiments of the present disclosure.

FIG. 3 is a block diagram of an image generator according to some embodiments of the present disclosure. It should be noted that the image generator described below is merely provided for illustrating an example, and not intended to limit the scope of the present disclosure.

As illustrated in FIG. 3, the image generator 105 may include, a radiation module 310, an image processing module 320, a control module 330, and a storage module 340. The radiation module 310 may include an X-ray generating unit 311 and an X-ray detecting unit 312. In some embodiments, the control module 330 may control the X-ray generating unit 311 and/or the X-ray detecting unit 312 of the radiation module 310, the image processing module 320, and/or the storage module 340. The image processing module 320 may process information received from the radiation module 310, the control module 330, and/or the storage module 340. The image processing module 320 may generate one or more CT images based on the information and deliver the images for display. The storage unit 340 may store information received from the image processing module 320, the control module 330, and/or the radiation module 310. The radiation module 310, the control module 330, the image processing module 320, and the storage module 340 may be connected with each other directly, or with an intermediate unit (not shown in FIG. 3). The intermediate unit may be a visible component or an invisible field (radio, optical, sonic, electromagnetic induction, etc.). The connection between different units may be wired or wireless. The wired connection may include using a metal cable, an optical cable, a hybrid cable, an interface, or the like, or any combination thereof. The wireless connection may include using a Local Area Network (LAN), a Wide Area Network (WAN), a Bluetooth, a ZigBee, a Near Field Communication (NFC), or the like, or any combination thereof. It should be noted that the above description about the radiation system is merely an example, should not be understood as the only embodiment. Obviously, to those skilled in the art, after understanding the basic principles of the connection between different units, the units and connection between the units may be modified or varied without departing from the principles. The modifications and variations are still within the scope of the current disclosure described above. In some embodiments, these units may be independent, and in some embodiments, part of the units may be integrated into one unit to work together.

The radiation module 310 may scan an object (not shown in FIG. 3) under examination and generate the raw data of an X-ray image. The object may include a substance, a tissue, an organ, a specimen, a body, a human being, or the like, or any combination thereof. In some embodiments, the object may include a head, a breast, a lung, a pleura, a mediastinum, an abdomen, a long intestine, a small intestine, a bladder, a gallbladder, a triple warmer, a pelvic cavity, a backbone, extremities, a skeleton, a blood vessel, or the like, or any combination thereof. The X-ray generating unit 311 may generate X-rays to traverse the object under examination. The X-ray generating unit 311 may include an X-ray generator, a high-voltage generator, and/or other accessories. The X-ray generator may include one or more X-ray tubes. An X-ray tube may emit X-rays. The X-ray generating unit 311 may be a cold cathode ion tube, a high vacuum hot cathode tube, a rotating anode tube, etc. The emitted X-ray beams may take the form of a line, a narrow pencil, a narrow fan, a fan, a cone, a wedge, or the like, or an irregular shape, or any combination thereof. An X-ray tube in the X-ray generating unit 311 may be fixed at a location. An X-ray tube may be translated or rotated in some scenarios.

The X-ray detecting unit 312 may receive the X-rays emitted from the X-ray generating unit 311 or other radiation source. The X-rays from the X-ray generating unit 311 may traverse the object under examination, and then reach the X-ray detecting unit 312. After receiving the X-rays, the X-ray detecting unit 312 may generate the raw data of an X-ray image of the object under examination. The term "raw data" may refer to the data that may be detected by the X-ray detecting unit 312, and the data may be utilized to construct an X-ray image. The X-ray detecting unit 312 may receive X-rays and generate the raw data of an X-ray image of the object under examination. The X-ray detecting unit 312 may include an X-ray detector or other components. The shape of the X-ray detector may be flat, arc-shaped, circular, or the like, or any combination thereof. The fan angle of the arc-shaped detector may be an angle from 0° to 360°. The fan angle may be fixed or adjustable according to different conditions including, for example, the desired resolution of an image, the size of an image, the sensitivity of a detector, the stability of a detector, or the like, or any combination thereof. In some embodiments, the pixels of the detector may be the number of the smallest detecting units, e.g., the number of scintillator or photosensor, etc. The pixels of the detector may be arranged in a single row, two rows, or another number of rows. The X-ray detector may be one-dimensional, two-dimensional, or three-dimensional.

The control module 330 may control the radiation module 310, the image processing module 320, the storage module 340, or other units or devices in the system according to some embodiments of the present disclosure. The control module 330 may receive information from or send information to the radiation module 310, the image processing module 320, and/or the storage module 340. In some embodiments, the control module 330 may control the radiation module 310 to generate a certain voltage, and/or a certain current for a scanning of an object. Merely by way of example, the voltage and/or current may be different for examining people of different age, weight, height, or so forth. In some embodiments, the control module 330 may receive a command provided by, e.g., a user, an imaging technician, or a doctor. Exemplary commands may include a scanning time, a location of the object, or a rotating speed of the gantry, or the like, or any combination thereof. The control module 330 may control the image processing module 320 to select different algorithms to process the raw data of an X-ray image. The control module 330 may select a protocol among multiple protocols that are designed for various scan scenarios. The control module 330 may transmit some commands to the storage module 340 to retrieve images for display. Exemplary commands may include the size of an image, the portion of an object, or the duration of an X-ray image to be displayed on a display screen. In some embodiments of the present disclosure, an X-ray image may be divided into several sub-portions for display. The control module 330 may control the division of the X-ray image. For example, the control module 330 may determine the number of sub-portions to be generated, the size of a sub-portion, the region to be covered in a sub-portion, or the like, or any combination thereof. It should be noted that the above description about the control module is merely an example according to the present disclosure.

The image processing module 320 may process different kinds of information received from different modules or units including the radiation module 310, the control module 330, the storage module 340, or other modules or units that may generate information. The image processing module 320 may process the data from the radiation module 310 to generate an X-ray image of an object under examination. Image processing may be based on an algorithm including, for example, Fourier slice theorem, filtered back projection algorithm, fan-beam reconstruction, iterative reconstruction, or the like, or any combination thereof. The image processing module 320 may transfer the information from the storage module 340 to a particular form that may be identified by the control module 330, and it may process the information from the control module 130 to adjust the storage module 340. The information from the control module 330 to the radiation module 310 may be processed by the image processing module 320 firstly so that it can be identified. The above description of the image processing module 320 is merely for exemplary purposes, should not be understood as the only embodiments, and these examples do not limit the scope of the present disclosure.

The storage module 340 may store information. The information may include programs, software, algorithms, data, text, number, images, voice, or the like, or any combination thereof. For example, a user or an operator may input some initial parameters or conditions to initiate a scan that may be stored in the storage module 340. Exemplary parameters or conditions may include the scanning time, the location of the object for scanning, the rotating speed of the gantry, or the like, or any combination thereof. As another example, some information may be imported from external resource, such as a floppy disk, a hard disk, a wireless terminal, or the like, or any combination thereof. The storage module 340 may receive the information from the control module 330 to adjust some parameters relating to display. Said parameters may include, but are not limited to the size of an image, the portion of an object where image is to be displayed, or the duration that an image remains on a display screen. In respect to the display of the X-ray images, the whole or part of an X-ray image may be displayed. In some embodiments, an X-ray image may be divided into several sub-portions, which may be display on a screen at the same time or in a certain order. And according to some embodiments of the present disclosure, the user or the operator may select one or more sub-portions to display according to some conditions. Merely by way of example, the user may specify that an enlarged view of a sub-portion is to be displayed. It should be noted that the above description about the storage module 340 is merely an example according to some embodiments of the present disclosure.

It should be noted that the above description of the image generator 105 of the X-ray imaging system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the assembly and/or function of the image generator 105 may be varied or changed according to specific implementation scenarios. Merely by way of example, some other components may be added into the image generator 105, such as a patient positioning unit, a high-voltage tank, an amplifier unit, a storage unit, an analog-to-digital converter, a digital-to-analog converter, an interface circuit, or the like, or any combination thereof. The amplifier unit may amplify signals received by the X-ray detecting unit 312. Note that the X-ray imaging system may be a singlemodality imaging system, or a multi-modality imaging system including, e.g., a positron emission tomography-computed tomography (PET-CT) system, a computed tomography-magnetic resonance imaging (CT-MRI) system, a remote medical X-ray imaging system, etc.

Figure 4A:
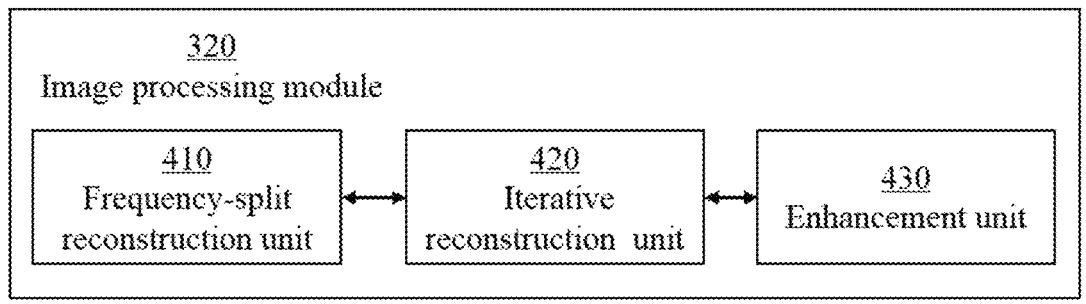
FIG. 4A is a block diagram of an image processing module according to some embodiments of the present disclosure.

FIG. 4A is a block diagram of the image processing module 320 according to some embodiments of the present disclosure. As shown in the figure, the image processing module 320 may include a frequency-split reconstruction unit 410, an iterative reconstruction unit 420, and an enhancement unit 430. The data received by the image processing module 320 may be sent to the frequency-split reconstruction unit 410, the iterative reconstruction unit 420, and/or the enhancement unit 430.

The frequency-split reconstruction unit 410 may treat raw data generated by scanning an object. The low-frequency component and the high-frequency component of the raw data may be treated separately in the analysis unit. In some embodiments, to treat the low-frequency component of the raw data, the analysis unit may generate an image on a region relating to an ROI (or referred to as an ROI related region). The analysis unit may perform a forward projection on the image within the ROI related region to obtain a modified sinogram. A low-pass filter may then be applied to the modified sinogram to obtain the low-frequency component. To treat the high-frequency component of the raw data, a high-pass filter may be applied to the raw data to obtain the high-frequency component.

As used herein, a low-pass filter may be a filter that passes signals with a frequency lower than a certain cutoff frequency and attenuates signals with frequencies higher than the cutoff frequency. In some embodiments, the cutoff frequency may be 5 lp/cm (line pair per centimeter) or below. In some other embodiments, the cutoff frequency may be 4 lp/cm or below. In some embodiments, the cutoff frequency may be 3 lp/cm or below. In some embodiments, the cutoff frequency may be 2 lp/cm or below. A transient spectrum of length 1 to 3 lp/cm may be present in the low-pass filter. As used herein, a high-pass filter may be a filter that passes signals with a frequency higher than a certain cutoff frequency and attenuates signals with frequencies lower than the cutoff frequency. In some embodiments, the cutoff frequency may be 2 lp/cm or above. In some other embodiments, the cutoff frequency may be 3 lp/cm or above. In some embodiments, the cutoff frequency may be 4 lp/cm or above. In some embodiments, the cutoff frequency may be 5 lp/cm or above. In some embodiments, the low-pass filter may have a narrow width in the space domain. As used herein, a narrow spatial width for the low-pass filter may indicate that the spatial width of the low pass filter is much less than the size, or the characteristic dimension, of the region of interest. For example, the analysis unit may include a low pass filter of Gauss type. In some embodiments, the low-pass filter and the high-pass filter may form an all-pass filter.

Figure 4B:
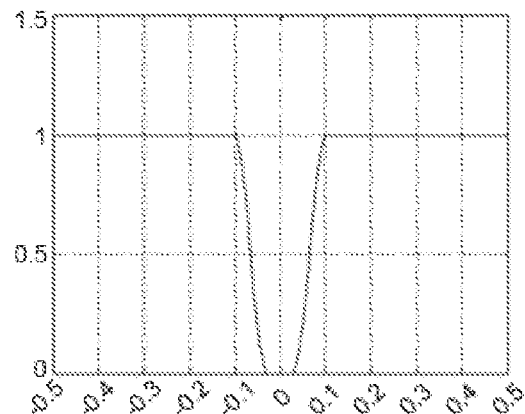
FIGS. 4B and 4C give an exemplary high pass filter in the frequency domain and the time domain, respectively according to some embodiments of the present disclosure.
Figure 4C:
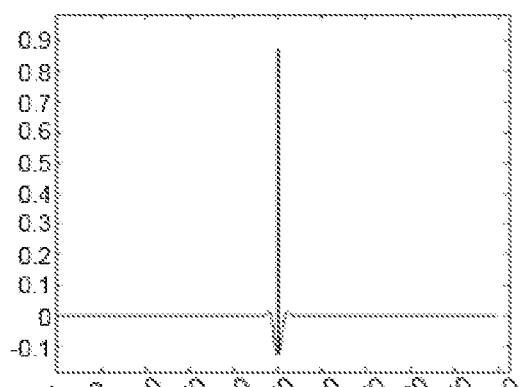

FIGS. 4B and 4C provide the curves obtained using an exemplary high pass filter in the frequency domain and the time domain, respectively. The spatial width of the exemplary high pass filter used to obtain the results shown in FIG. 4C is no more than one tenth of the characteristic response time of the high pass filter The narrowness of the spatial width for the high pass filter may indicate that the effect of the high pass filter on the region of interest is of local nature.

Figure 4D:
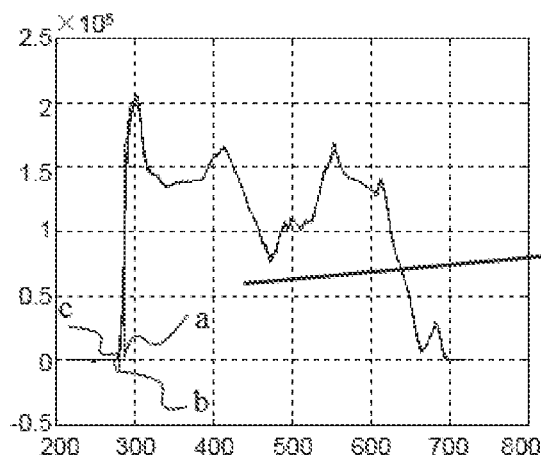
FIGS. 4D and 4E illustrate the effect of various exemplary low pass filters on raw data according to some embodiments of the present disclosure.
Figure 4E:
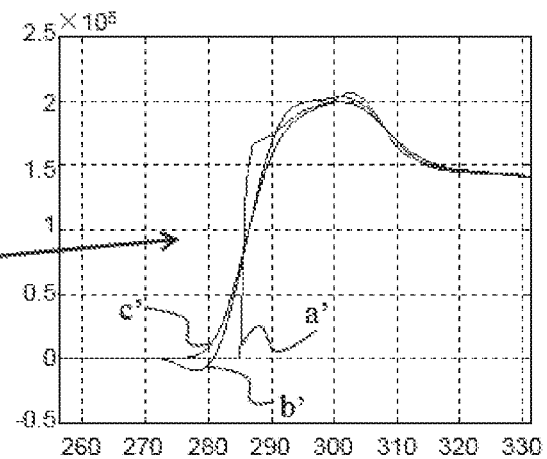

FIGS. 4D and 4E illustrate the effect of various exemplary low pass filters on raw data FIG. 4E is a rescaled presentation of the data of FIG. 4D. In FIG. 4E, the curve a shows the raw data generated by applying the filtered back projection (FBP) on a CT image. The curves b and c show the results generated by applying various exemplary low pass filters on the raw data a, respectively. The curve b exhibits the phenomenon of Gibbs artifact by bending down below zero before rising up to follow the curve a. The curve c does not have the "bending down" phenomenon as in the curve b.

The iterative reconstruction unit 420 may synthesize the processed low-frequency component and high-frequency component of the raw data. Further, the iterative reconstruction unit 420 may apply a reconstruction method to obtain a CT image in a region related to the ROI. The reconstruction method may include, for example, Fourier slice theorem, filtered back projection algorithm, fan-beam reconstruction, iterative reconstruction, etc. In some embodiments of the present disclosure, the iterative reconstruction unit 420 may perform forward projection and backward projection iteratively until a desired image is generated. In respect to the forward projection, contribution factor and voxel value may be calculated to determine the contribution of the voxels.

The iterative reconstruction unit 420 may reduce the noise of images generated by the frequency-split reconstruction unit 410. Exemplary algorithms of noise reduction may be based on a noise model. In some embodiments, an algorithm of noise reduction may include chroma and luminance noise separation, a linear smoothing filter, anisotropic diffusion, a non-local means, a nonlinear filter, wavelet transform, a statistical algorithm, or the like, or any combination thereof. In some embodiments of the present disclosure, a noise model may be constructed to reduce the noise of the images generated by the frequency-split reconstruction unit 410. A weighting parameter may be set in the noise model to measure the usefulness of the data with noise. For example, data with a high level of noise may be given a lower weight, whereas data with a low level of noise may be given a higher weight. The weight of the data may be utilized to indicate the usability of the data, so that the data of higher weight may be used more frequently. In some embodiments, a penalty data may be introduced in the noise model to control the noise of the image during the process of regularization. The penalty data may be obtained from a regularization based on either the initial image or the updated image during the iterations. As described herein, the regularization may characterize an inherent property of the CT system and preserve some characteristics within the image. Exemplary characteristics may include the sharp edge between a high intensity region and a low intensity region. In some embodiments, the regularization may help enhance the quality of the image by, for example, improving the smoothness within a high intensity region or a low intensity region. In some embodiments, the regularization may distinguish regions with different intensity. For example, the regularization may be helpful in understanding the position of a metal implant inside the body of a patient. The regulation may increase the visibility of a sharp edge between the metal and a non-metal tissue. It may produce an image of a uniform distribution of noise. In some embodiments, some banding artifacts and streaking artifacts caused by the high level of noise may be suppressed using the method illustrated above.

It should be noted that the above description of the image processing unit is provided for the purposes of illustration, not intended to limit the scope of the present disclosure. For persons having ordinary skills in the art, various variations and modifications may be conducted under the teaching of the present disclosure. However, those variations and modifications may not depart the protecting scope of the present disclosure. For example, the data acquired by the data acquisition unit may be sent to the frequency-split reconstruction unit 410, the iterative reconstruction unit 420, and the enhancement unit 430 either concurrently or sequentially.

Figure 5:
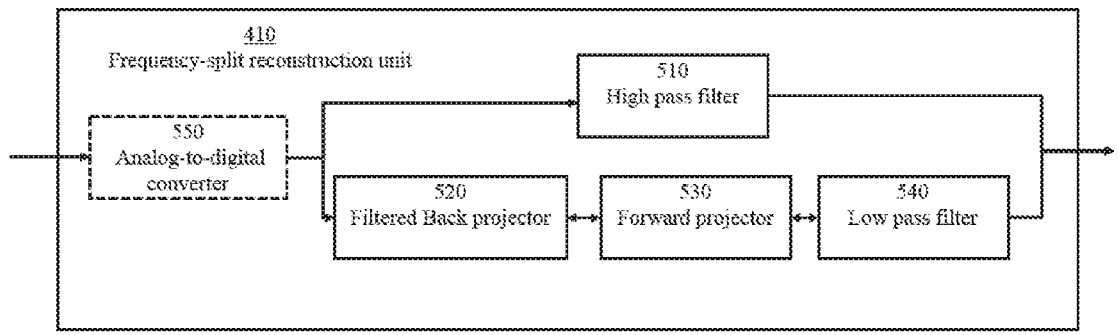
FIG. 5 is a block diagram of a frequency-split reconstruction unit according to some embodiments of the present disclosure.

FIG. 5 is a block diagram of the frequency-split reconstruction unit 410 according to some embodiments of the present disclosure. As shown in the figure, the frequency-split reconstruction unit 410 may include a high pass filter 510, a filtered filtered back projector 520, a forward projector 530, and a low pass filter 540. The raw data, or the sinogram received by the frequency-split reconstruction unit 410 may be split and processed separately into the high-frequency part and the low-frequency part. The raw data received may be sent to the high pass filter 510, and the filtered filtered back projector 520. In some embodiments of the present disclosure, the frequency-split reconstruction unit 410 may include an analog-to-digital converter (ADC) 550. The ADC 550 may convert the raw data detected by the detector into digital values.

The high pass filter 510 may be applied to the raw data to obtain the high-frequency component of the raw data. The high pass filter 510 may be a one-dimensional filter. In some embodiments, the high-pass filter may be a two-dimensional filter. In the case of a one-dimensional filter, the high pass filter may be applied along the detector channels. In some embodiments, the high-pass filter may have a narrow width in the space domain, or have an effectively narrow width in the space domain. For example, the high-pass filter may be a Gauss type filter. For another example, the high-pass filter may be an atan type filter. In some embodiments, the high-pass filter may be designed directly by designating a desired response curve in the frequency domain. The frequency domain is used in the analysis of signals with respect to frequency, rather than time or space domain. In some embodiments, Fourier transform may be utilized to transform a signal in the time or space domain into the counterpart in the frequency domain. The response curve of the high-pass filter expressed in the frequency domain may exhibit various behavior of the filter with respect to the frequency. In some embodiments, the high pass filter may be obtained by removing a low pass filter from an all pass filter. In some embodiments, the width or effective width of the response curve in the space domain may be such that raw data or sinogram may be processed by the high-pass filter locally, and that the filtered data may be insensitive to the background.

The filtered back projector 520 may process the raw data or sinogram to generate intermediate images in a certain region of an FOV. For example, the filtered back projector 520 may generate an intermediate image in the region of interest (ROI) within an FOV. As another example, the filtered back projector 520 may generate an intermediate image in a region containing or enclosing the region of interest (ROI). The algorithm applied by the filtered back projector 520 may be an algebraic/analytic image reconstruction algorithm. Examples of such reconstruction algorithms may include one based on filtered back projection (FBP) reconstruction, Feldkamp-Davis-Kress (FDK) reconstruction, maximum a posteriori probability (MAP), maximum likelihood (ML), algebraic reconstruction technique (ART), entropy-based optimization, least squares (LS) or penalized weighted least squares (PWLS), single domain noise reduction algorithm, or the like, or a combination thereof. The described algorithms may be executed once, or may be executed more than once.

The forward projector 530 may process the intermediate images generated by filtered back projector 520 to produce intermediate sinograms. The forward projector 530 may be a forward projector acting on a local image instead of the image on the whole FOV. For example, the forward projector may act on the ROI. As another example, the forward projector may act on a ROI related region. For example, the ROI related region may contain the region of interest, and the ROI may be a portion or a subarea of the ROI related region. As another example, the ROI related region may contain the region of interest, and may have a similar shape compared to the ROI, and larger than the ROI by a scaling factor (see, for example, FIG. 10A for an illustration, where the ROI related region is the region defined by the outer boundary, whereas the region of interest is the region within the inner boundary. These two regions are self-similar with respect to the origin O, and the scaling factor is a positive number $\alpha > 1$.)

The low pass filter 540 may be applied to the intermediate sinograms generated by the forward projector 530 to obtain the low-frequency component of the intermediate sinograms. The low pass filter 540 may be a one-dimensional filter. In some embodiments, the low-pass filter may be a two-dimensional filter. In the case of one-dimensional filter, the low pass filter may be applied along the detector channels. In some embodiments, the low-pass filter may have a narrow width in the space domain, or have an effectively narrow width in the space domain. For example, the low-pass filter may be a Gauss type filter. As another example, the low-pass filter may be an atan type filter. In some embodiments, the high pass filter 510 and the low pass filter 540 may form an all-pass filter. The width or effective width in the space domain may be narrow such that raw data or a sinogram may be processed by the low-pass filter locally, thus the filtered data may be insensitive to the background.

It should be noted that the block diagram described above is provided for the purposes of illustration, not intended to limit the scope of the present disclosure. For persons having ordinary skills in the art, various variations and modifications may be conducted under the teaching of the present disclosure. However, those variations and modifications may not depart from the scope of the present disclosure.

Figure 6:
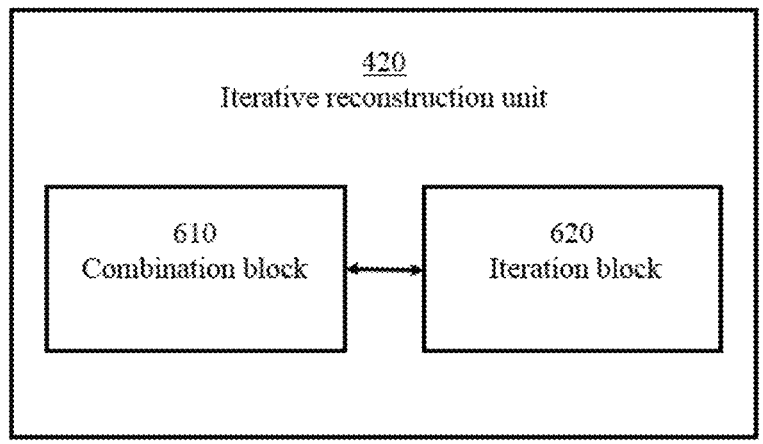
FIG. 6 is a block diagram of an iterative reconstruction unit according to some embodiments of the present disclosure.

FIG. 6 is a block diagram of the iterative reconstruction unit according to some embodiments of the present disclosure. As shown in the figure, the iterative reconstruction unit may include a combination block 610, and an iteration block 620. The combination block 610 may combine received sinograms. The combination may be achieved by way of an addition of the received sinograms. See, for example, FIG. 8 and the description thereof.

The iteration block 620 may process the sinogram generated by the combination block 610. In some embodiments, an iterative reconstruction (IR) algorithm may be applied in the iteration block 620 to the sinogram generated by the combination block 610, so as to generate an image in a ROI related region of FOV. For example, the ROI related region may be the ROI itself. As another example, the ROI related region may be a region containing the ROI. As a further example, the ROI related region may be a region surrounding or containing the region of interest. The reconstruction may include an iterative reconstruction process that may include a computer based iterative processing. The iterative reconstruction process may include iterative projection, noise reduction or elimination, etc. The above mentioned examples of models are provided for illustration purposes and not intended to limit the scope of the present disclosure.

It should be understood that the exemplary block diagram described above are provided for the purposes of illustration, and not intended to limit the scope of the present disclosure. For persons having ordinary skills in the art, various variations and modifications may be conducted under the teaching of the present disclosure. However, those variations and modifications may not depart from the scope of the present disclosure.

In the process of image reconstruction, for the sinogram of a ROI related region, high-frequency components of the sinogram and the low-frequency components of the sinogram may be reconstructed separately. For example, the low-frequency components of the sinogram of a ROI related region may be reconstructed by an analytic and/or algebraic method. The analytical method may be a filtered back projection (FBP) method. As another example, the high-frequency components of the sinogram of a ROI related region may be reconstructed by an iterative method. The iterative method utilized this way may improve photon utilization and/or spatial resolution.

In so doing the reconstruction of the high frequency component may need to be based mostly on local projection data associated with the region related to the ROI. This may substantially reduce the need to include the complete projection dataset for the full FOV and the whole object in the iterative reconstruction (IR) algorithm, as used in the iteration block 620.

Figure 7:
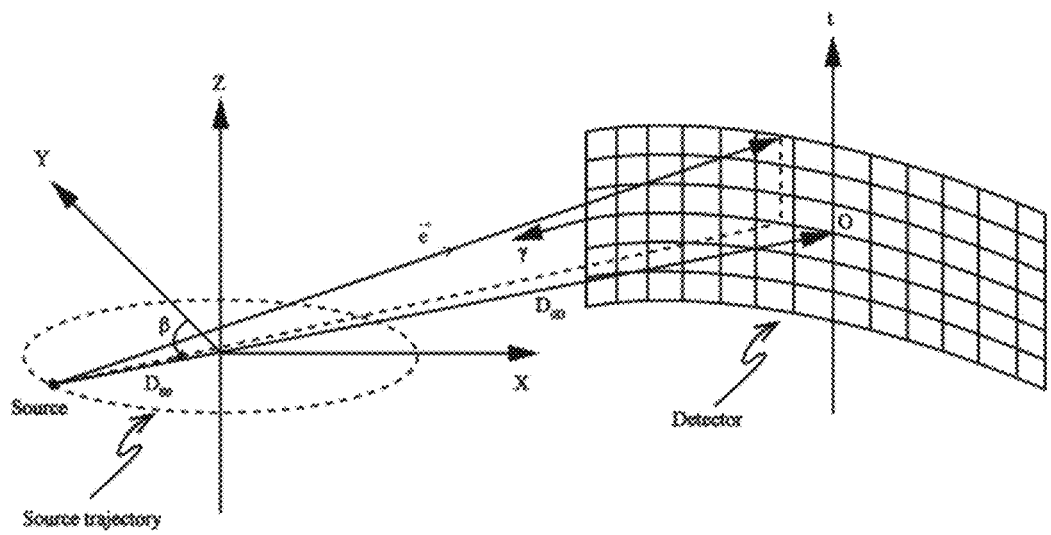
FIG. 7 is a diagram illustrating an exemplary axial cone-beam flat-detector geometry according to some embodiments of the present disclosure.

FIG. 7 is a diagram illustrating an exemplary axial cone-beam flat-detector geometry according to some embodiments of the present disclosure. Here the trajectory of the source may be a circle lying on the plane where the z-coordinate may be zero. The image reconstruction may be performed using the cone-beam formed by the beam emanating from the source and shedding on the surface formed by the detectors. As illustrated in FIG. 7, the t-direction of the detector surface coincides with the direction of the z-axis. The y-direction of the detector surface is along the circumferential direction of the gantry for CT imaging system.

Figure 8:
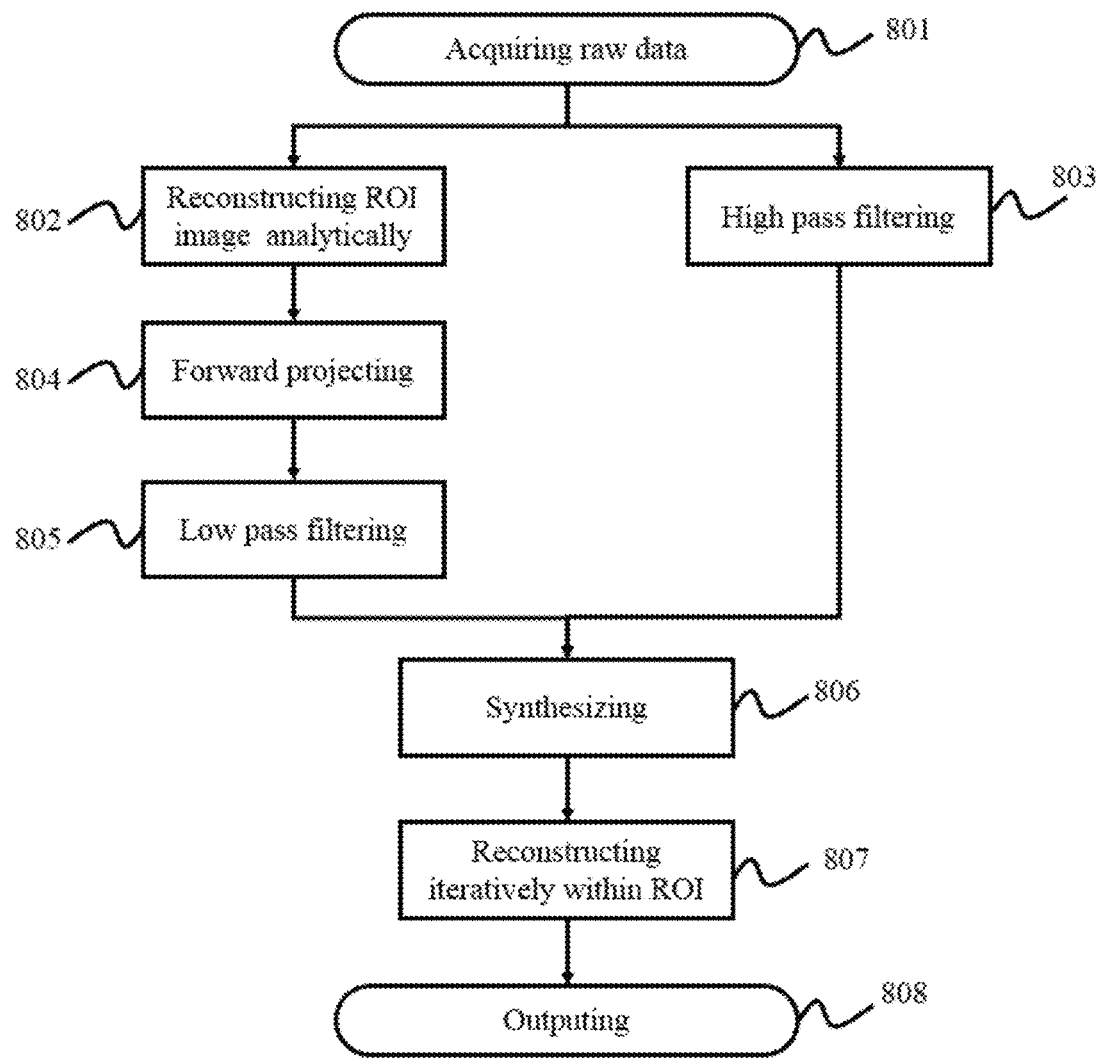
FIG. 8 is a flowchart illustrating an exemplary process of frequency-split iterative reconstruction according to some embodiments of the present disclosure.

FIG. 8 illustrates an exemplary flowchart of a process for image reconstruction according to some embodiments of the present disclosure. An original sinogram, or raw data, may be acquired in step 801 through, for example, a data scan process in step 203. At least two different processing routes may be conducted based on the raw data acquired in step 801. As described, the raw data in 801 may be obtained by scanning an object in step 203. The object may be a human body, an X-ray-safe item whose inner structure required to be imaged non-invasively or non-destructively (e.g., an antique, an instrument, etc.), or the like. Alternatively, the raw data may be obtained from other resources, e.g., a computer-simulated scan, an on-line database, an off-line database. The online-database may include a cloud-server type database.

An initial reconstruction algorithm may be performed in step 802 based on the original sinogram acquired in step 801, in which an initial ROI-related image may be generated. Examples of such reconstruction algorithms may include those based on filtered back projection (FBP) reconstruction, Feldkamp-Davis-Kress (FDK) reconstruction, maximum a posteriori probability (MAP), maximum likelihood (ML), algebraic reconstruction technique (ART), entropy-based optimization, least squares (LS) or penalized weighted least squares (PWLS), a single domain noise reduction algorithm, or the like, or a combination thereof. The described algorithms may be executed once, or may be executed iteratively.

In some embodiments, the initial image may also be approximated based on a setting including, for example, a default setting in the system, a template from a template library, etc. For example, the initial image may be a CT image in the ROI. In some embodiments, the initial image may be a CT image in a ROI related region related to the ROI. For example, the ROI related region may contain the region of interest. As another example, the ROI related region may contain a template from a template library containing the region of interest, wherein the template may have a specific configuration or shape. The template library may include a plurality of templates for a ROI related region relating to an ROI. For instance, the plurality of templates may have various configurations or shapes based on, for example, the size of an ROI, the shape of an ROI, the type of tissue of an ROI, the type of material of an ROI (metal, plastic, wood, etc.), a patient-related health or personal information, the type or model of the scanning device or a portion thereof, or the like, or a combination thereof. Exemplary types of tissue of an ROI may include the organ from which the ROI is selected, a tumorous tissue, a tissue of a specific type of tumor, or the like, or a combination thereof. Exemplary patient-related health or personal information may include the gender of a patient, the race of a patient, the age, the weight of a patient, the stature of a patient, the health history of a patient, a confirmed or suspect disease, or the like, or a combination thereof.

In step 804, the initial image in the ROI related region related to ROI generated in step 802 may then be subject to a forward projector. For example, the forward projector may act on the ROI. As another example, the forward projector may act on a ROI related region relating to the ROI. For example, the ROI related region may contain the region of interest. As another example, the ROI related region may contain a template from a template library containing the region of interest, wherein the template may have specific configuration or shape.

In step 805, a low-pass filter may be applied to the sinogram generated by the forward projector. The low-pass filter may be a one-dimensional filter. In some embodiments, the low-pass filter may be a two-dimensional filter. In the case of one-dimensional filter, the low pass filter may be applied along the detector channels. In some embodiments, the low-pass filter may have a narrow width in the space domain, or have an effectively narrow width in the space domain. For example, the low-pass filter may be a Gauss type filter. As another example, the low-pass filter may be an atan type filter. In some embodiments, the low-pass filter may be designed directly by designating a desired response curve in the frequency domain. The frequency domain is used in the analysis of signals with respect to frequency, rather than time or space domain. In some embodiments, Fourier transform may be utilized to transform a signal in the time or space domain into the counterpart in the frequency domain. The response curve of the low-pass filter expressed in the frequency domain may exhibit various amplitude and/or phase behavior of the filter with respect to the frequency. In some embodiments, the low pass filter may be obtained by removing a high pass filter from an all pass filter. In some embodiments, the width or effective width of the response curve in the space domain may be such that raw data or sinogram may be processed by the low-pass filter locally, and that the filtered data may be insensitive to the background. The narrowness of width or effective width in the space domain ensures that local data may be considered more, and the filtered data may not be sensitive to the background outside the ROI related region related to the ROI.

In step 803, a high-pass filter may be applied to the original sinogram. The high-pass filter may be a one-dimensional filter. In some embodiments, the high-pass filter may be a two-dimensional filter. In the case of one-dimensional filter, the high pass filter may be applied along the detector channels. In some embodiments, the high-pass filter and the low-pass filter in step 805 may combine to form an all-pass filter. In some embodiments, the high-pass filter may have a narrow width in the space domain, or have an effectively narrow width in the space domain. In some embodiment, the spatial width of the high pass filter may be 20% or less of the size, or the characteristic dimension, of the region of interest. In some other embodiments, the spatial width of the high pass filter may be 10% or less of the size, or the characteristic dimension, of the region of interest. For example, the high-pass filter may be a Gauss type filter. For another example, the high-pass filter may be an atan type filter. In some embodiments, a high-pass filter may be obtained by removing a low-pass filter from an all-pass filter. The width or effective width in the space domain of the high-pass filter may be narrow such that local data may be considered more, and the filtered data may be insensitive to the background outside the ROI related region related to the ROI.

The tuning of the low-pass filter and the high-pass filter may be determined based on parameters including, for example, the geometry of the region of interest, the geometry of the ROI related region related to ROI, or the like, or a combination thereof. For example, the cutoff frequency of the low-pass and/or the high-pass filter may be within a suitable interval. If the cutoff frequency is set too low, then too much information from the analytic/algebraic reconstruction as in step 802 may be lost. If the cutoff frequency is set too high, then high frequency information may be lost, resulting in deteriorated images and/or a poor spatial resolution.

In step 806, a synthesized sinogram combining the result from step 805 and that from step 803 may be generated by way of, for example, an addition of the sinograms from step 805 and step 803. In some embodiments, a linear combination of the sinograms from step 805 and step 803 may be utilized. For example, weighting factors may be applied to the results from step 805 and 803, respectively, and the weighted addition of the sinograms may be generated. These weighting factors may be constants, or variable in at least one execution of the algorithm.

In step 807, an iterative reconstruction (IR) algorithm may be applied to the ROI related region related to the ROI. The CT image within the ROI related region related to ROI may be generated. The reconstruction may include an iterative reconstruction process. The iterative reconstruction process may include iterative projection, noise reduction/elimination, etc. The above mentioned examples of models are provided for illustration purposes and not intended to limit the scope of the present disclosure.

In step 808, the resulted image in the ROI related region related to ROI may be then output. The image may be provided to the doctor, or to the patient, or any relevant person. The image may be provided to a display device, a printer, a database, or the like, or a combination thereof. The database may be an online-database, or an off-line database. The online database may be a cloud based database.

It shall be noticed that many alternatives, modifications, and variations will be apparent to those skilled in the art. The features, structures, methods, and other characteristics of the exemplary embodiments described herein may be combined in various ways to obtain additional and/or alternative exemplary embodiments. For example, it shall be appreciated to those skilled in the art that the analytical/algebraic reconstruction steps 802 and the forward projection steps 804 may be repeated for several times before performing the low pass filtering process 805. For another example, some calibration and/or normalization steps may be inserted after step 803 to reduce the noise in the resulted sinogram, before synthesizing with the sinogram generated from the low pass filtering process in step 805.

The frequency-split algorithm to generate an image in the region of interest as illustrated above in FIG. 8 may be further modified to incorporate the treatment of artifacts, which may be caused by the interference between the sharp change of sinogram data near the boundary of ROI and the dominance domain of the low-pass filter. In a real-time application, the sinogram data near the boundary of ROI may undergo a sharp change. Such a sharp change may be deformed severely by the operation of a low-pass filter (an exemplary effect of a high pass filter on the raw data may be seen in FIG. 4D or FIG. 4E), leading to some artifacts near the boundary of the ROI (see, for example, FIG. 13A for an illustration for such an artifact near the boundary of ROI). To accommodate for this interference between the sharp change of sinogram data near the boundary of an ROI and the effect of the low-pass filtering, the image area to be processed may be extended beyond the ROI.

Figure 9:
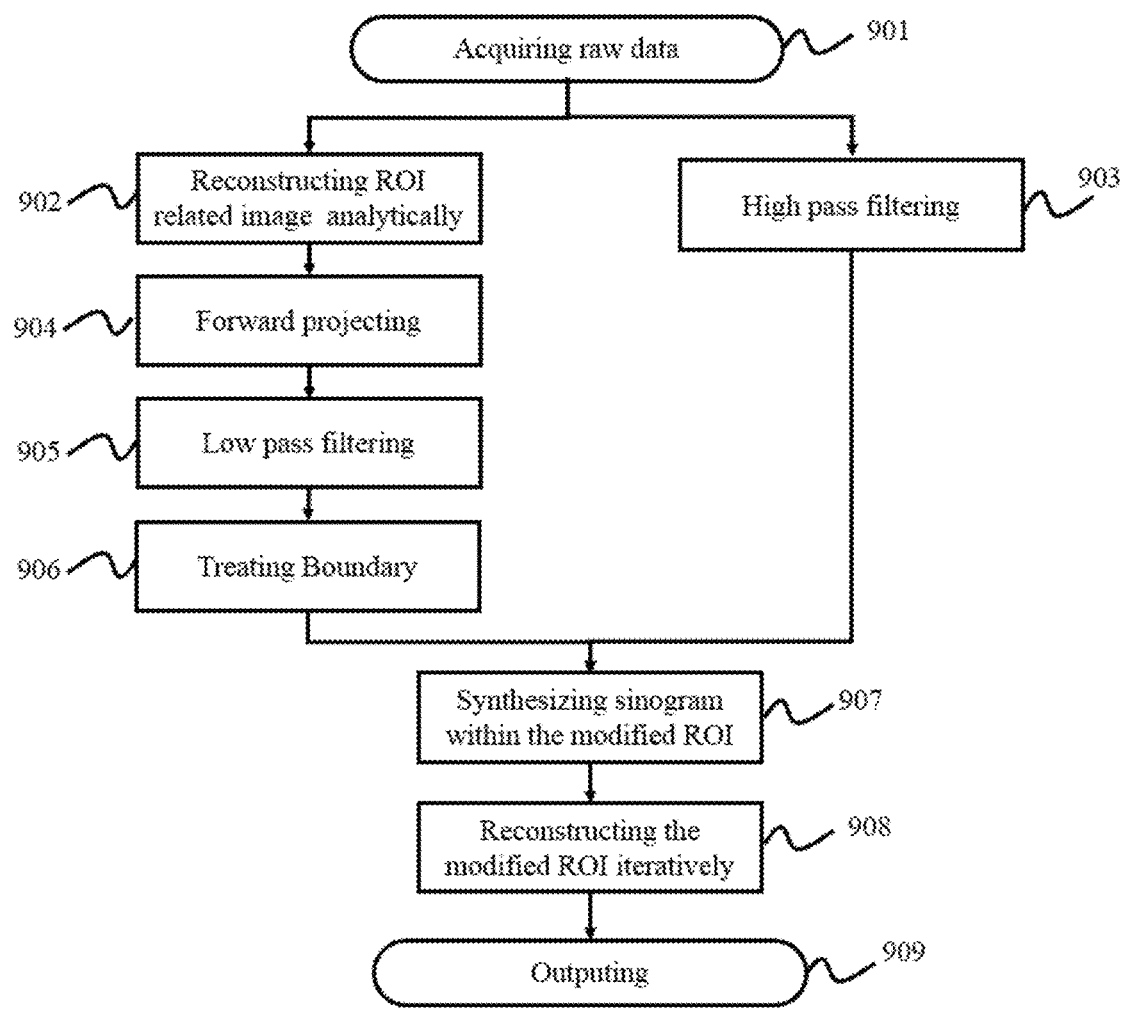
FIG. 9 is a flowchart illustrating an exemplary process of frequency-split iterative reconstruction according to some embodiments of the present disclosure.

FIG. 9 illustrates an exemplary flowchart of a process for image reconstruction according to some embodiments of the present disclosure. An original sinogram, or raw data, may be acquired in step 901 through, for example, a data scan process in step 203. At least two different processing routes may be conducted based on the raw data acquired in step 901. As described, the raw data in 901 may be obtained by scanning an object in step 203. The object may be a human body, an X-ray-safe item whose inner structure required to be imaged non-invasively or non-destructively (e.g., an antique, an instrument, etc.), or the like. Alternatively, the raw data may be obtained from other resources, e.g., a computer-simulated scan, an on-line database, an off-line database. The online-database may include a cloud-server type database.

An initial reconstruction algorithm may be performed in step 902 based on the original sinogram acquired in step 901, where at least two ROI-related images may be generated. One CT image may be constructed for the ROI, and at least another CT image may be constructed for a neighboring area (NA) surrounding the region of interest. The combination of the ROI and the neighboring area together may form an extended region of interest (EROI) containing the ROI. For example, the area A of ROI may be extended in a self-similar way to a larger area $\alpha A$, where $\alpha>1$ is a scaling factor. The neighboring area then may be given by $\alpha A \backslash A$, i.e., the part of $\alpha A$ devoid of A. See, for example, the shaded area in FIG. 10A, or the outer frame surrounding the shaded area in FIG. 10B. In some embodiments, the ROI is a rectangle A, then the rectangle A may be extended to a larger rectangle $\alpha A$ containing A, where $\alpha>1$ is a scaling factor. The neighboring area surrounding the region of interest may be then given by the annular-type frame, as illustrated in FIG. 10A and FIG. 10B. The choice of the scaling factor $\alpha$ may depend upon considerations including, for example, the spatial width of the low-pass filter, the spatial width of the high-pass filter, or the like, or a combination thereof. In some embodiments, the scaling factor $\alpha$ may be such that the distance between the outer boundary and the inner boundary of the neighboring area is larger than or equal to the spatial width of the low-pass filter. Merely by way of example, the distance between the outer boundary and the inner boundary of the neighboring area may be at least 15 mm, depending on, for example, the space-domain width of the low-pass filter and the size of the detector.

After two CT images have been constructed for the ROI and the NA, respectively, two images reconstructed for the extended ROI (EROI) may be generated in the following way. One image on the EROI may be generated by setting zero in the neighboring area of the ROI, while the image data in the ROI remain unchanged (see FIG. 10A for illustration). Another image on EROI may be generated by setting zero in the region of interest, while the image data in the NA remain unchanged (see FIG. 10B for illustration).

Examples of such reconstruction algorithms may include those based on filtered back projection (FBP) reconstruction, Feldkamp-Davis-Kress (FDK) reconstruction, maximum a posteriori probability (MAP), maximum likelihood (ML), algebraic reconstruction technique (ART), entropy-based optimization, least squares (LS) or penalized weighted least squares (PWLS), single domain noise reduction algorithm, or the like, or a combination thereof. The described algorithms may be executed once, or may be executed more than once.

In step 904, the at least two images on extended ROI generated in step 902 may then be subject to a forward projector For example, the forward projector may include the ROI. As another example, the forward projector may act on a ROI related region relating to the ROI. For example, the ROI related region may contain the region of interest. As another example, the ROI related region may contain the neighboring area of the region of interest. The extended region of interest may be obtained based on a scaling factor $\alpha$, where $\alpha>1$. The sinogram generated by the forward projector on the image in the extended ROI where the image data on the neighboring area being zero may be denoted as FP1. The sinogram generated by the forward projector on the image in the extended ROI where the image data in the region of interest being zero may be denoted as FP2.

In step 905, a low-pass filter may be applied to the combination of sinograms FP1 and FP2 generated in step 904. The combination of FP1 and FP2 may be an addition of FP1 and FP2. In some embodiments, the combination of FP1 and FP2 may be a linear combination of FP1 and FP2, i.e., aFP1+bFP2, where a, b may be the weighting factors including real constants. In some embodiments, a may be equal to 1, or b may be equal to 1. In some embodiments, a and b may both be equal to 1. In some embodiments, a and b may be constants of different values. In some embodiments, a and b may be constants of a same value. The low-pass filter may be a one-dimensional filter. In some embodiments, the low-pass filter may be a two-dimensional filter. In the case of one-dimensional filter, the low pass filter may be applied along the detector channels. In some embodiments, the low-pass filter may have a narrow width in the space domain, or have an effectively narrow width in the space domain. The distance between the inner boundary and the outer boundary of neighboring area surrounding the ROI may be larger than the spatial width of the low pass filter. For example, the low-pass filter may be a Gauss type filter. For another example, the low-pass filter may be an atan type filter. In some embodiments, the low pass filter may also be obtained by removing a high-pass filter from an all-pass filter. The width or effective width of the response curve for the low pass filter in the space domain may be narrow such that raw data or a sinogram may be processed by the low-pass filter locally, thus the filtered data may be insensitive to the background.

In step 906, the sinogram obtained in step 905 may be further treated by subtracting the sinogram FP2 from it. In some embodiments, the processes in steps 905 and 906 may be expressed as the following:

$$\text{Low-pass}(FP1+FP2)-FP2. \qquad (1)$$

In some embodiments, the processes in steps 905 and 906 may be expressed as the following:

$$\text{Low-pass}(aFP1+bFP2)-cFP2, \qquad (2)$$

where a, b, c may be weighting factors including real constants. For example, a, b, c may all be equal to one. In some embodiments, these constants may depend on the spatial width of the low-pass filter, or the size of the detectors.

In step 903, a high-pass filter may be applied to the original sinogram. The high-pass filter may be a one-dimensional filter. In some embodiments, the high-pass filter may be a two-dimensional filter. In the case of one-dimensional filter, the high pass filter may be applied along the detector channels. In some embodiments, the high-pass filter and the low-pass filter in step 905 may combine to form an all-pass filter. In some embodiments, the high-pass filter may have a narrow width in the space domain, or have an effectively narrow width in the space domain. For example, the high-pass filter may be a Gauss type filter. For another example, the high-pass filter may be an atan type filter. In some embodiments, a high-pass filter may be obtained by removing a low-pass filter from an all-pass filter.

The tuning of the low-pass filter and the high-pass filter may be determined based on parameters including, for example, the geometry of the region of interest, the geometry of the ROI related region related to ROI, or the like, or a combination thereof. For example, the cutoff frequency of the low-pass and/or the high-pass filter may be within a suitable interval. If the cutoff frequency is set too low, then too much information from the analytic/algebraic reconstruction as in step 902 may be lost. If the cut off frequency is set too high, then high frequency information may be lost, that leads to deteriorated image and poor spatial resolution.

In step 907, a synthesized sinogram combining result from step 906 and that from step 903 may be generated. The way of generating may be an addition of the sinograms from step 906 and step 903. In some embodiments, a linear combination of the sinograms from step 906 and step 903 may be utilized. For example, certain factors may be multiplied to the results from step 906 and 903, respectively, and the multiplied sinograms may be added together. These factors may be constants, or non-constants varying in each execution of the algorithm.

In step 908, an iterative reconstruction (IR) algorithm is applied to the synthesized sinogram to generate image for the extended ROI. The CT image within the ROI is thus generated. The reconstruction described may include an iterative reconstruction process that may comprise a computer based iterative processing. The iterative reconstruction process may comprise iterative projections and noise elimination processes, etc. The above mentioned examples of models are provided for illustration purposes and not intended to limit the scope of the present disclosure.

In step 909, the resulted image in the ROI may be then output. The image may be provided to the doctor, or to the patient, or any relevant person. The image may be provided to a display device, or output to a database. The database may be an online-database, or an off-line database. The online database may be a cloud based database.

It shall be noticed that many alternatives, modifications, and variations will be apparent to those skilled in the art. The features, structures, methods, and other characteristics of the exemplary embodiments described herein may be combined in various ways to obtain additional and/or alternative exemplary embodiments. For example, it shall be appreciated to those skilled in the art that the analytical/algebraic reconstruction steps 902 and the forward projection steps 904 may be repeated several times before performing the low pass filtering process 905. For another example, some calibration and/or normalization steps may be inserted after step 903 to reduce the noise in the resulted sinogram, before synthesizing with the sinogram generated from the low pass filtering process in step 905.

FIG. 11 is a block diagram of the image processing module 320A according to some embodiments of the present disclosure. As shown in the figure, the image processing module 320A may include a frequency-split reconstruction unit 410A, an iterative reconstruction unit 420A, a storage unit 430A, and a parallel co-processing unit 440A. The data received by the image processing module 320A may be sent to the frequency-split reconstruction unit 410A, iterative reconstruction unit 420A, the enhancement unit 430A, and/or the parallel co-processing unit 440A.

The frequency-split reconstruction unit 410A may treat raw data generated by scanning an object. The low-frequency component and the high-frequency component of the raw data may be processed separately in the analysis unit. In some embodiments, to process the low-frequency component of the raw data, the analysis unit may generate an image on a ROI related region. The analysis unit may perform a forward projection on the image restricted on the ROI related region to obtain a modified sinogram. A low-pass filter may then be applied to the modified sinogram to obtain the low-frequency component. A low-pass filter may be a filter that passes signals with a frequency lower than a certain cutoff frequency and attenuates signals with frequencies higher than the cutoff frequency. In some embodiments, the cutoff frequency may be 100 Hz or below. In some other embodiments, the cutoff frequency may be 80 Hz or below. In some embodiments, the cutoff frequency may be 60 Hz or below. In some embodiments, the cutoff frequency may be 40 Hz or below. To treat the high-frequency component of the raw data, a high-pass filter may be applied to the raw data to obtain the high-frequency component. A high-pass filter may be a filter that passes signals with a frequency higher than a certain cutoff frequency and attenuates signals with frequencies lower than the cutoff frequency. In some embodiments, the cutoff frequency may be 40 Hz or above. In some other embodiments, the cutoff frequency may be 60 Hz or above. In some embodiments, the cutoff frequency may be 80 Hz or above. In some embodiments, the cutoff frequency may be 100 Hz or above. In some embodiments, the low-pass filter may have a narrow width in the space domain. For example, the analysis unit may include a low pass filter of Gauss type. In some embodiments, the low-pass filter and the high-pass filter may form an all-pass filter.

The iterative reconstruction unit 420A may synthesize the processed low-frequency component and high-frequency component of the raw data. Further, the iterative reconstruction unit 420A may apply a reconstruction method to obtain a CT image in the region related to ROI. The reconstruction method may include, for example, Fourier slice theorem, filtered back projection algorithm, fan-beam reconstruction, iterative reconstruction, etc. In some embodiments of the present disclosure, the iterative reconstruction unit 420A may perform forward projection and backward projection iteratively until a desired image is generated. In respect to the forward projection, contribution factor and voxel value may be calculated to determine the contribution of the voxels.

It should be noted that the above description of the image processing unit is provided for the purposes of illustration, not intended to limit the scope of the present disclosure. For persons having ordinary skills in the art, various variations and modifications may be conducted under the teaching of the present disclosure. However, those variations and modifications may not depart the protecting scope of the present disclosure.

Figure 12:
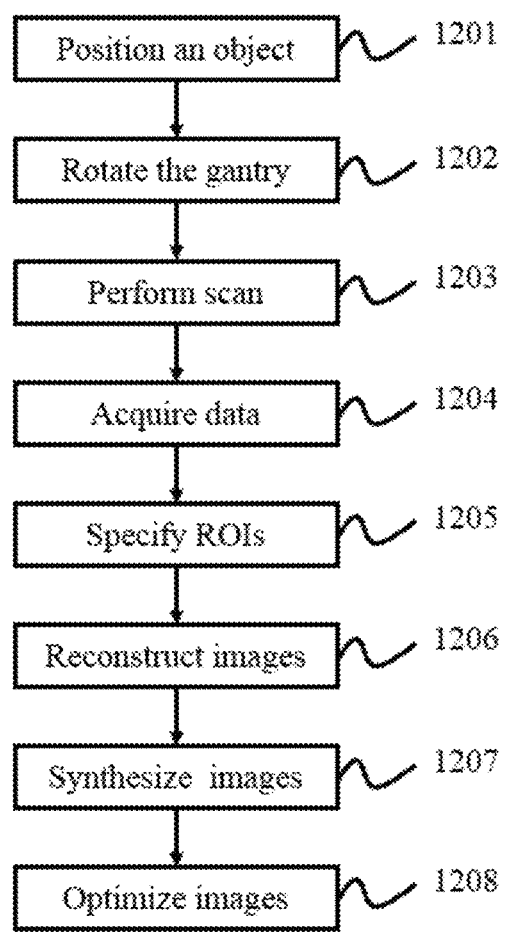
FIG. 12 is a flowchart illustrating a process of a CT scan according to some embodiments of the present disclosure.

FIG. 12 is a flowchart illustrating an imaging process according to some embodiments of the present disclosure. In step 1201, an object may be positioned in the X-ray imaging system 100, specifically, on the patient table 102 that is described elsewhere in the present disclosure. Merely by way of example, the object may include a substance, a tissue, an organ, a specimen, a body, or the like, or any combination thereof. In some embodiments, the object may include a head, a breast, a lung, a pleura, a mediastinum, an abdomen, a long intestine, a small intestine, a bladder, a gallbladder, a triple warmer, a pelvic cavity, a backbone, extremities, a skeleton, a blood vessel, or the like, or any combination thereof.

After the object is positioned, the gantry of the X-ray imaging system 100 may be rotated to a desired position in step 1202.

In step 1203, a scan may be performed on the object. In some embodiments of the present disclosure, a number of protocols may be created for scanning different objects. Multiple parameters may be determined by the protocols. Merely by way of example, the parameters may include a collimator aperture, a detector aperture, X-ray tube voltage and/or current, a scan mode, a table index speed, a gantry speed, a reconstruction field of view (FOV), or the like, or any combination thereof.

By way of the scan, the raw data corresponding to the object may be acquired in step 1204. Before treating the raw data generated in step 1204, various regions related to the region of interest (ROI) may be determined. For example, a neighboring area of ROI may be specified. For another example, various ROIs may be specified. These ROIs may be overlapping or non-overlapping.

After the raw data is acquired, the images of the object on various ROIs may be reconstructed in step 1206. Merely by way of example, the reconstruction of the images may be based on methods including Fourier slice theorem, filtered back projection algorithm, fan-beam reconstruction, iterative reconstruction, etc.

In step 1207, an image including various ROIs may be generated based on the parallel co-processing of the images in various ROIs. The image reconstructed in step 1207 may be output in step 1208. The output image may undergo further process, such as noise reduction, contrast enhancement, etc.

It should be noted that the flowchart described above is provided for the purposes of illustration, and not intended to limit the scope of the present disclosure. For persons having ordinary skills in the art, various variations and modifications may be conduct under the teaching of the present disclosure. However, those variations and modifications may not depart from the protecting of the present disclosure.

EXAMPLES

The following examples are provided for illustration purposes, and not intended to limit the scope of the present disclosure.

FIG. 13A and FIG. 13B are two X-ray images that were generated based on frequency-splitting and the combination of analytic reconstruction and iterative reconstruction according to some embodiments of the present disclosure. FIG. 13A and FIG. 13B may be generated according to the process illustrated in FIG. 8.

FIG. 14A and FIG. 14B are two X-ray images that were generated based on frequency-splitting and the combination of analytic reconstruction and iterative reconstruction according to some embodiments of the present disclosure. FIG. 14A may be generated according to the process illustrated in FIG. 8. FIG. 14B may be generated according to the process illustrated in FIG. 9. The difference between FIG. 14A and FIG. 14B may be discerned by noting that in FIG. 14A, some artifact near the left hand side boundary of region of interest may be seen clearly. On the other hand, the artifact near the left hand side boundary of region of interest in FIG. 14B has been alleviated due to a specific choice of extended region of interest, and the effect that the spatial width of the low-pass filter and/or the high-pass filter is less than or equal to the distance between the outer boundary of the extended region of interest and the boundary of the region of interest.

As will be also appreciated, the above described method embodiments may take the form of computer or controller implemented processes and apparatuses for practicing those processes. The disclosure can also be embodied in the form of computer program code containing instructions embodied in tangible media, such as floppy diskettes, CD-ROMs, hard drives, or any other computer-readable storage medium, wherein, when the computer program code is loaded into and executed by a computer or controller, the computer becomes an apparatus for practicing the invention. The disclosure may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

It should be noted that the above description is merely provided for the purposes of illustration, and not intended to limit the scope of the present disclosure. For persons having ordinary skills in the art, multiple variations and modifications may be made under the teachings of the present disclosure. For example, the non-Cartesian sampling disclosed in this disclosure may combine with techniques including parallel imaging, compressed sensing, partial Fourier transformation, or the like, or any combination thereof. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties such as molecular weight, reaction conditions, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on at least one machine each of which has at least one processor and at least one storage device, the method comprising:
    receiving a set of raw data relating to a subject generated by an imaging device;
    determining a region of interest (ROI) in a field of view (FOV) of the imaging device;
    determining an extended ROI in the FOV of the imaging device;
    reconstructing a first image corresponding to the extended ROI based on the set of raw data;
    performing forward projection on the first image to obtain a first sinogram;
    applying a first filter on the first sinogram to obtain a third sinogram;
    applying a second filter on the set of raw data to obtain a fifth sinogram;
    performing, based on the third sinogram and the fifth sinogram, iterative reconstruction to generate a third image; and
    extracting a fourth image corresponding to the ROI from the third image.

2. The method of claim 1, wherein the first set of raw data comprises sinogram data.

3. The method of claim 1, wherein the reconstructing a first image corresponding to the extended ROI based on the set of raw data comprises:
    applying filtered back projection (FBP) on the set of raw data.

4. The method of claim 1, wherein the ROI is rectangular, and the ROI has a first width and a first height.

5. The method of claim 4, wherein the extended ROI is rectangular, and the extended ROI has a second width and a second height.

6. The method of claim 5, wherein the ratio of the first width to the first height is the same as the second width to the second height.

7. The method of claim 5, wherein the ratio of the second width to the first width or the ratio of the second height to the first height has a positive correlation with a size of the first filter.

8. The method of claim 1, wherein the first filter is a low pass filter.

9. The method of claim 8, wherein the first filter is a Gauss filter, an atan filter, or a filter configured to provide a desired response curve in a frequency domain.

10. The method of claim 1, wherein the first filter and the second filter together form an all-pass filter.

11. A non-transitory computer readable medium, comprising at least one set of instructions, wherein when executed by at least one processor of a computing device, the at least one set of instructions cause the at least one processor to effectuate a method comprising:
    receiving a set of raw data relating to a subject generated by an imaging device;
    determining a region of interest (ROI) in a field of view (FOV) of the imaging device;
    determining an extended ROI in the FOV of the imaging device;

reconstructing a first image corresponding to the extended ROI based on the set of raw data;

performing forward projection on the first image to obtain a first sinogram;

applying a first filter on the first sinogram to obtain a third sinogram;

applying a second filter on the set of raw data to obtain a fifth sinogram;

performing, based on the third sinogram and the fifth sinogram, iterative reconstruction to generate a third image; and extracting a fourth image corresponding to the ROI from the third image.

12. The medium of claim 11, wherein the ROI is rectangular, and the ROI has a first width and a first height.

13. The medium of claim 12, wherein the extended ROI is rectangular, and the extended ROI has a second width and a second height.

14. The medium of claim 13, wherein the ratio of the first width to the first height is the same as the second width to the second height.

15. The medium of claim 11, wherein the first filter is a low pass filter.

16. A system comprising:
at least one storage device storing a set of instructions; and
at least one processor in communication with the at least one storage medium, wherein when executing the set of instructions, the at least one processor is configured to cause the system to:

receive a set of raw data relating to a subject generated by an imaging device;

determine a region of interest (ROI) in a field of view (FOV) of the imaging device;

determine an extended ROI in the FOV of the imaging device;

reconstruct a first image corresponding to the extended ROI based on the set of raw data;

perform forward projection on the first image to obtain a first sinogram;

apply a first filter on the first sinogram to obtain a third sinogram;

apply a second filter on the set of raw data to obtain a fifth sinogram;

perform, based on the third sinogram and the fifth sinogram, iterative reconstruction to generate a third image; and extract a fourth image corresponding to the ROI from the third image.

17. The system of claim 16, wherein the ROI is rectangular, and the ROI has a first width and a first height.

18. The system of claim 17, wherein the extended ROI is rectangular, and the extended ROI has a second width and a second height.

19. The system of claim 18, wherein the ratio of the first width to the first height is the same as the second width to the second height.

20. The system of claim 16, wherein the first filter is a low pass filter.

* * * * *